(12) United States Patent
Kamiya et al.

(10) Patent No.: US 7,781,536 B2
(45) Date of Patent: Aug. 24, 2010

(54) HIGHLY OXYGEN-PERMEABLE HYDRATED OCULAR LENS

(75) Inventors: Takehisa Kamiya, Tokyo (JP); Kazunori Kobayashi, Tokyo (JP); Kenji Uno, Tokyo (JP)

(73) Assignee: Seed Co., Ltd., Tokyo (JP)

( * ) Notice: Subject to any disclaimer, the term of this patent is extended or adjusted under 35 U.S.C. 154(b) by 532 days.

(21) Appl. No.: 11/663,525

(22) PCT Filed: Sep. 15, 2005

(86) PCT No.: PCT/JP2005/017012

§ 371 (c)(1),
(2), (4) Date: Mar. 21, 2007

(87) PCT Pub. No.: WO2006/035611

PCT Pub. Date: Apr. 6, 2006

(65) Prior Publication Data

US 2008/0094570 A1 Apr. 24, 2008

(30) Foreign Application Priority Data

Sep. 30, 2004 (JP) .............................. 2004-287014
Aug. 23, 2005 (JP) .............................. 2005-241090

(51) Int. Cl.
 *C08C 19/42* (2006.01)
(52) U.S. Cl. ...................... 525/369; 525/383; 525/384; 525/479; 351/160 H; 351/159; 623/4.1; 623/6.11; 623/6.56; 623/6.59
(58) Field of Classification Search ................. 525/383, 525/384, 369, 479; 351/160 H, 159; 623/4.1, 623/6.11, 6.56, 6.59
See application file for complete search history.

(56) References Cited

U.S. PATENT DOCUMENTS

| | | | | |
|---|---|---|---|---|
| 4,954,586 A | * | 9/1990 | Toyoshima et al. | 526/245 |
| 2004/0054106 A1 | * | 3/2004 | Ito et al. | 526/279 |
| 2004/0186248 A1 | * | 9/2004 | Vanderlaan et al. | 525/474 |

FOREIGN PATENT DOCUMENTS

| | | |
|---|---|---|
| JP | 3-160009 A | 7/1991 |
| JP | 3-228014 A | 10/1991 |
| JP | 5-164995 A | 6/1993 |
| JP | 7-196745 A | 8/1995 |
| JP | 7-239458 A | 9/1995 |
| JP | 8-292403 A | 11/1996 |
| JP | 8-304746 A | 11/1996 |
| JP | 2001-311917 | 11/2001 |
| JP | 2002-513948 A | 5/2002 |
| JP | 2003-268055 A | 9/2003 |
| WO | WO 00/70388 | 11/2000 |

* cited by examiner

*Primary Examiner*—Vasu Jagannathan
*Assistant Examiner*—Robert C Boyle
(74) *Attorney, Agent, or Firm*—Frommer Lawrence & Haug LLP; Ronald R. Santucci

(57) ABSTRACT

It is an object of the present invention to provide an ocular lens superior in the wettability of the surface thereof, hydrating properties, oxygen permeability, flexibility, elasticity, transparency and shape recoverability though it has a composition using a silicone-containing monomer. The present invention relates to a highly oxygen-permeable hydrated ocular lens obtained by saponifying a copolymer prepared from a specific both-terminal (meth)acryl polydimethylsiloxane, a vinyl carboxylate, a (meth)acrylamide type monomer, a vinyl type crosslinking agent, one or both of a (meth)acrylate having a tertiary structure and a (meth)acrylate having a cyclic structure as (meth)acrylates each having a bulky structure at its side chain and a monomer copolymerizable with these compounds.

4 Claims, No Drawings

HIGHLY OXYGEN-PERMEABLE HYDRATED OCULAR LENS

This application is a 371 of PCT/JP2005/017012 filed on Sep. 15, 2005, published on Apr. 6, 2006 under publication number WO 2006/035611 A1 which claims priority benefits from Japanese Patent Application Number 2004-287014 filed Sep. 30, 2004 and Japanese Patent Application Number 2005-241090 filed Aug. 23, 2005.

TECHNICAL FIELD

The present invention relates to a highly oxygen-permeable hydrated ocular lens. The present invention relates, particularly, to a hydrated ocular lens, such as a hydrated soft contact lens and intraocular lens, having the characteristics that it has an outstandingly highly wettable surface and is superior, oxygen permeability, flexibility, elasticity, transparency, shape recoverability and mechanical strength.

BACKGROUND ART

As the hydrated soft contact lens, there are hydrated polymers containing a hydrophilic monomer such as 2-hydroxyethylmethacrylate and vinyl pyrrolidone as their major components. The hydrated soft contact lens is known to have a good wearing feel due to the flexibility of the material thereof. Also, it is known that the oxygen permeability of the hydrated soft contact lens is generally dependent on the moisture content of the lens. However, in the case of a polymer primarily using vinyl pyrrolidone which is a highly hydrated soft contact lens material as its major component, its oxygen transmission coefficient is about $50 \times 10^{-11}$ $(cm^2/sec) \cdot (mLO_2/mL \times mmHg)$ even if the moisture content is 80% and it is not therefore said that oxygen is supplied in a sufficient amount to the cornea. Also, since the lens is highly hydrated, it is easily contaminated, causing a deterioration in wearing feel and the angle of vision when it is used for a long period of time. Specifically, the conventional hydrated soft contact lens has insufficient oxygen permeability though it has a good wearing feel, giving rise to, for example, the problem that the cornea is put into an oxygen deficient state, causing the onset of grave symptoms.

Because the continuous wearing of a contact lens is the main current in recent years, high oxygen permeability is a necessary and essential element and further, higher wettability of the surface of the lens is desired to exhibit soil resistance which can stand against continuous wearing. If a silicone type monomer is used as a lens raw material, it causes the lens to be highly hydrophilic, though high oxygen permeability is obtained. Therefore, because the lens is caused to be highly hydrophobic, it becomes cloudy when it is utilized for a hydrated soft contact lens and it is hardly avoidable to drop the moisture content of the lens. As a result, the raw material itself is hardened, causing a deteriorated wearing feel and also, the surface of the lens to exhibit deteriorated wettability, which is eventually a cause of a dry feel and the deposition of soils contained in lachrymal components.

In the case of a hydrated contact lens using a silicone type monomer, under this situation, there are large problems as to a proper moisture content and an improvement in the wettability of the surface of the lens. Therefore, there are various proposals concerning materials used for silicone-containing hydrated contact lenses having high oxygen permeability and wettability.

There is a disclosure of, for example, technologies in which a silicone hydrogel contact lens comprising a silicone macromonomer, a bulk polysiloxanyl(meth)acrylate monomer and a lactam-containing monomer is subjected to plasma surface treatment and then, hydrated (see, Patent Reference 1). However, this method has, for example, the problems that it needs very large-scaled equipment such as a plasma treating apparatus and that it is complicated in the design of conditions for forming a film.

There is also a disclosure concerning an ocular lens material obtained by copolymerizing a polysiloxane prepolymer capped with an acryl group, a bulk polysiloxanyl(meth)acrylate monomer and a hydrophilic monomer (see Patent Reference 2). This material is obtained in the form of a low modulus hydrophilic gel by combining two different silicone components, that is, a polysiloxane prepolymer and a bulk polysiloxane type monomer. This material has a moisture content of about 17 to 43% and an oxygen transmission coefficient of about 60 to $150 \times 10^{-11}$ $(cm^2/sec) \cdot (mLO_2/mL \times mmHg)$. Since this material has a low modulus, posing the problem of the stability of the shape of a lens and also, it is not said that sufficient consideration is given to the wettability of the surface of the lens.

In the meantime, an ocular lens material comprising a siloxane-containing polymer obtained by polymerizing a siloxane macromonomer with a lower fatty acid vinyl ester (see Patent Reference 3) and an ocular lens material comprising a macromer having a polysiloxane at its side chain (see Patent Reference 4) are disclosed as non-hydrated ocular lenses having flexibility and shape recoverability. The siloxane macromonomer which is a major component in these ocular lenses has a urethane group in each structure and imparts mechanical strength, flexibility and wettability. However, a urethane bond is hydrolyzed relatively easily and it is therefore estimated that when this siloxane macromonomer is used in a large amount for use as a hydrated ocular lens, the polymer becomes cloudy and is deteriorated in the function as an ocular lens. Also, when the amount of the siloxane macromonomer to be used is reduced, a polymer having entirely satisfactory oxygen permeability is not obtained. Also, if the siloxane bond part in a molecule is increased to improve oxygen permeability, the compatibility with other copolymer components is deteriorated, so that a polymer which is transparent and has good mechanical strength is not obtained and it is therefore difficult to use as an ocular lens.

Patent Reference 1: Japanese Patent Application National Publication (Laid-Open) No. 2002-513948
Patent Reference 2: Japanese Patent Application Laid-Open (JP-A) No. 2003-268055
Patent Reference 3: W/O 00/70388
Patent Reference 4: JP-A No. 13-311917

DISCLOSURE OF THE INVENTION

In the case of a hydrated contact lens having high oxygen permeability, it is most effective to improve the raw material itself in order to make the lens have good flexibility and elasticity and to improve the wettability of the lens without any deterioration in wearing feel and soil resistance.

It is an object of the present invention to provide an ocular lens superior in the wettability and hydrating properties of the surface thereof, oxygen permeability, flexibility, elasticity, transparency and shape recoverability though the lens has a composition using a siloxane-containing monomer.

Further, the present invention can provide an ocular lens which has an oxygen transmission coefficient of about 100 to $200 \times 10^{-11}$ $(cm^2/sec) \cdot (mLO_2/mL \times mmHg)$, is superior in the wettability of the surface thereof, tensile strength and rupture extension and prevents its strength from being decreased by boiling sterilization or chemical sterilization.

(1) The present invention relates to a highly oxygen-permeable hydrated ocular lens obtained by saponifying a copolymer prepared from a both-terminal (meth)acryl polydimethylsiloxane represented by the following formula (1), a vinyl carboxylate, a (meth)acrylamide type monomer and a monomer copolymerizable with these compounds.

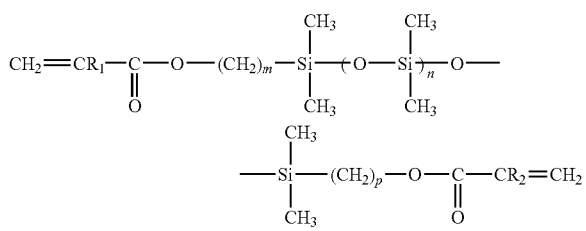

wherein $R_1$ and $R_2$ respectively represent a hydrogen atom or a methyl group, m and p respectively denote an integer from 1 to 5 and n denotes an integer from 10 to 150.

(2) Also, the present invention relates to a highly oxygen-permeable hydrated ocular lens obtained by saponifying a copolymer prepared from a both-terminal (meth)acryl polydimethylsiloxane represented by the above formula (1), a vinyl carboxylate, a (meth)acrylamide type monomer, a vinyl type crosslinking agent and a monomer copolymerizable with these compounds.

(3) Also, the present invention relates to a highly oxygen-permeable hydrated ocular lens obtained by saponifying a copolymer prepared from a both-terminal (meth)acryl polydimethylsiloxane represented by the above formula (1), a vinyl carboxylate, a (meth)acrylamide type monomer, one or both of a (meth)acrylate having a tertiary structure and a (meth)acrylate having a cyclic structure as (meth)acrylates having a bulky structure at its side chain and a monomer copolymerizable with these compounds.

(4) Further, the present invention relates to a highly oxygen-permeable hydrated ocular lens obtained by saponifying a copolymer prepared from a both-terminal (meth)acryl polydimethylsiloxane represented by the above formula (1), a vinyl carboxylate, a (meth)acrylamide type monomer, a vinyl type crosslinking agent, one or both of a (meth)acrylate having a tertiary structure and a (meth)acrylate having a cyclic structure as (meth)acrylates having a bulky structure at its side chain and a monomer copolymerizable with these compounds.

According to the present invention, an ocular lens can be provided relatively easily which has good wettability of the surface thereof, oxygen permeability, transparency and shape recoverability, and is also superior in tensile strength and rupture extension.

BEST MODE FOR CARRYING OUT THE INVENTION

The both-terminal (meth)acryl polydimethylsiloxane used in the present invention is represented by the formula (1). Since this compound has two (meth)acryl groups at both terminals, it is highly reactive. However, if it is used in a usual way, the polymer exhibits hydrophobic properties and it is therefore difficult to handle this compound. Particularly, when n is too small, the elasticity and oxygen permeability of the polymer are deteriorated, whereas when n is too large, the hydrophobic properties of the polymer is too strong, which is a cause of a cloudy ocular lens. Therefore, in the present invention, n is an integer from 10 to 150 and m and p are respectively an integer from 1 to 5.

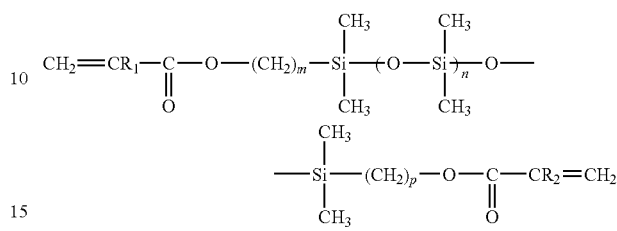

The amount of the both terminal (meth)acrylpolydimethylsiloxane is preferably 5 to 60 parts by weight and more preferably 10 to 40 parts by weight. If the content of the both terminal (meth)acrylpolydimethylsiloxane is less than 5 parts by weight, the oxygen permeability of the obtained polymer is deteriorated whereas if the content exceeds 60 parts by weight, the flexibility, hydrating properties and wettability of the surface of the polymer as the ocular lens are deteriorated, and therefore, such a content out of the above range is undesirable.

Examples of the vinyl carboxylate include vinyl acetate, vinyl propionate, vinyl butylate, vinyl laurate, vinyl stearate, vinyl(meth)acrylate, vinyl crotonate, vinyl benzoate and vinyl cinnamate. In the case of the present invention, saturated carboxylic acids such as vinyl acetate, vinyl propionate, vinyl lactate, vinyl laurate and vinyl stearate are preferably used.

The amount of the vinyl carboxylate is preferably 30 to 80 parts by weight and more preferably 40 to 70 parts by weight. If the content of the vinyl carboxylate is less than 30 parts by weight, this is undesirable because in the case where the obtained polymer is used for an ocular lens, not only the flexibility and hydrating properties of the lens are deteriorated but also the wettability of the surface of the lens is deteriorated. If the content exceeds 80 parts by weight, this is undesirable because the oxygen permeability of the polymer is deteriorated so that the features of the present invention cannot be exhibited.

One of the characteristics of the present invention is the formulation of the (meth)acrylamide type monomer. Specifically, the vinyl carboxylate part and this acrylamide part in the polymer largely contribute to the hydrating properties and the wettability of the surface. The present invention intends to raise the ability of retaining the wettability of the surface of the lens by carrying out selective saponification of the vinyl carboxylate contained in the polymer to saponify not only the surface of the lens but also the inside of the lens. In order to progress the saponification of the inside of the lens promptly without hydrolyzing other ester parts, it is necessary to swell the polymer promptly. For this, a fixed amount of an acrylamide type monomer is formulated. This renders it possible to carry out more effective treatment than in the case of using only the vinyl carboxylate, leading to the development of excellent characteristics. Examples of the (meth)acrylamide type monomer include N-dialkyl(meth)acrylamides such as N-methyl(meth)acrylamide, N-ethyl(meth)acrylamide, N-n-propyl(meth)acrylamide and N-isopropyl(meth)acrylamide and N,N-dialkyl(meth)acrylamides such as N,N-dimethyl(meth)acrylamide, N,N-diethyl(meth)acrylamide, N,N-methyl(ethyl)(meth)acrylamide and N,N-methyl(propyl)(meth)

acrylamide. In the case of the present invention, N,N-dialkyl (meth)acrylamides are preferably used and N,N-dimethylacrylamide is more preferable.

The amount of the acrylamide type monomer to be formulated is preferably 1 to 20 parts by weight and more preferably 5 to 15 parts by weight. If the content of N,N-dimethylacrylamide is less than 1 part by weight, the reactivity of saponification in the inside of the lens is deteriorated and therefore, it takes time to provide good hydrating properties and wettability of the surface of the lens, so that ester parts other than the vinyl carboxylate are hydrolyzed. For example, the (meth) acryl group of the both terminal (meth)acryl polydimethylsiloxane proceeds with hydrolysis, bringing about dissociation of the silicone unit, resulting in a deterioration in oxygen permeability, strength and flexibility. Also, if the content exceeds 20 parts by weight, the obtained polymer becomes cloudy by the influence of the compatibility with and hydrolysis of the both terminal (meth)acrylpolydimethylsiloxane and these phenomena are undesirable as a lens material.

In the present invention, a polyfunctional crosslinking component may be copolymerized to more improve heat resistance and mechanical properties. Examples of the crosslinking component include (meth)acrylate type crosslinking agents such as ethylene glycol di(meth)acrylate, diethylene glycol di(meth)acrylate, trierythlene glycol di(meth)acrylate, propylene glycol di(meth)acrylate, dipropylene glycol di(meth)acrylate, trimethylolpropanetri(meth) acrylate, pentaerythritol tri(meth)acrylate, pentaerythritol tetra(meth)acrylate and dipentaerythritol hexa(meth)acrylate and vinyl type crosslinking agents having a vinyl group or allyl group, such as allylmethacrylate, diallyl maleate, diallyl fumarate, diallyl succinate, diallyl phthalate, triallyl cyanurate, triallyl isocyanurate, diethylene glycol bisallylcarbonate, triallyl phosphate, triallyl trimellitate, diallyl ether, N,N-diallylmelamine and divinylbenzene.

In the case of the present invention, the both terminal (meth)acryl polydimethylsiloxane is a difunctional component and a crosslinking effect is therefore expected if the amount of the both terminal (meth)acryl polydimethylsiloxane to be formulated is increased. However, in the case of using a crosslinking component, a vinyl type crosslinking agent is preferable taking the polymerization reactivity of the vinyl carboxylate into account. More preferably, triallyl isocyanurate.

In the case of using a crosslinking component, the amount of the crosslinking component to be formulated is preferably in a range from 0.1 to 5 parts by weight and more preferably 0.1 to 3 parts by weight. When the amount of the crosslinking component is less than 0.1 parts by weight, the effect of the crosslinking component is not found whereas when the amount of the crosslinking component exceeds 5 parts by weight, the flexibility and elasticity of the obtained polymer are deteriorated because of an excessive crosslinking density, which is undesirable as a lens material.

In addition to the above components, various copolymerizable monomers are properly selected as desired in the present invention.

Although optional (meth)acrylates may be properly selected for various copolymerizable monomers to impart high oxygen permeability and wettability, the amount of the (meth)acrylate to be formulated is preferably within 20 parts by weight and more preferably within a range from 5 to 15 parts by weight.

Preferable examples of the (meth)acrylate type monomer include long-chain (meth)acrylates and (meth)acrylates having a bulky structure at their side chains. The copolymer of the present invention has a vinyl alcohol unit. However, there is the case where this part causes a reduction in tensile strength in a specified direction which is originated from a polyvinyl alcohol type material. Though its exact reason is not clarified, it is considered that when the long-chain (meth)acrylate and/or the (meth)acrylate having a bulky structure at its side chain are formulate, molecular orientation due to a polyvinyl alcohol unit is hindered and an improvement in practical strength can be therefore expected.

Although the long-chain (meth)acrylate and the (meth) acrylate having a bulky structure at its side chain produces its effect even if these components are formulated singly, both components may be formulated in each specified amount.

Examples of the long-chain (meth)acrylate include (meth) acrylates having about 4 to 20 carbon atoms. Specific examples of the long-chain (meth)acrylate include butyl (meth)acrylate, pentyl(meth)acrylate, hexyl(meth)acrylate, 2-ethylhexyl(meth)acrylate, heptyl(meth)acrylate, octyl (meth)acrylate, nonyl(meth)acrylate, decyl(meth)acrylate, dodecyl(meth)acrylate, lauryl(meth)acrylate, tridecyl(meth) acrylate, tetradecyl(meth)acrylate, 3-methyltridecyl(meth) acrylate, 6-methyltridecyl(meth)acrylate, 7-methyltridecyl (meth)acrylate, 2,11-dimethyldodecyl(meth)acrylate, 2,7-dimethyl-4,5-diethyloctyl(meth)acrylate, pentadecyl(meth) acrylate and stearyl(meth)acrylate.

In the present invention, particularly, lauryl(meth)acrylate and tridecyl(meth)acrylate are preferably used in view of handling characteristics. The amount of the (meth)acrylate to be formulated is preferably 1 to 20 parts by weight and more preferably 3 to 15 parts by weight. When the content is less than 1 part by weight, a large improvement in the physicochemical characteristics of the obtained polymer is not found and therefore a desired effect is not produced, which is undesirable. Also, if the content exceeds 20 parts by weight, the characteristics primarily intended in the present invention cannot be developed.

Examples of the (meth)acrylate having a bulky structure at its side chain include (meth)acrylates having a tertiary structure and/or (meth)acrylates having a cyclic structure.

Specific examples of the (meth)acrylate include tertiary butyl(meth)acrylate, tertiary butylcyclohexyl(meth)acrylate, phenyl(meth)acrylate, phenoxyethyl(meth)acrylate, benzyl (meth)acrylate, cyclohexyl(meth)acrylate, 2-tertiarybutylcyclohexyl(meth)acrylate, 3-tertiarybutylcyclohexyl(meth) acrylate, 4-tertiarybutylcyclohexyl(meth)acrylate, 2-secondarybutylcyclohexyl(meth)acrylate, 4-secondarybutylcyclohexyl(meth)acrylate, 2,4-di-tertiarybutylcyclohexyl (meth)acrylate, 2,4-di-secondarybutylcyclohexyl(meth) acrylate, 4-tertiaryamylcyclohexyl(meth)acrylate, 2,4-di-tertiaryamylcyclohexyl(meth)acrylate, 4-tertiaryoctylcyclohexyl(meth)acrylate, 4-(1-cyclohexyl-ethyl)-cyclohexyl(meth)acrylate, 4-(1-methyl-1-cyclohexyl-ethyl)cyclohexyl(methacrylate, nonylcyclohexyl(meth)acrylate and dodecylcyclohexyl(meth)acrylate.

In the present invention, tertiary butyl(meth)acrylate, benzyl(meth)acrylate and cyclohexyl(meth)acrylate are particularly preferably used in view of handling characteristics.

The amount of the methacrylate to be formulated is 1 to 10 parts by weight and preferably 3 to 8 parts by weight. If the amount is less than 1 part by weight, a desired effect is not obtained, whereas if the amount exceeds 10 parts by weight, the oxygen permeability and flexibility of the lens material are significantly deteriorated and therefore, an amount out of the above range is undesirable.

The methacrylate may be properly mixed with other copolymer components prior to use to the extent that the effect of the present invention is not hindered. The amount of the copolymer components to be formulated to the extent that the effect of the present invention is not hindered is within 20 parts by weight as shown above. Specifically, it is preferable to use the long-chain (meth)acrylate, the (meth)acrylate having a bulky structure at its side chain and other copolymer components in a total amount less than 20 parts by weight.

Examples of the alkyl(meth)acrylate as the above other polymer component include methyl(meth)acrylate, ethyl (meth)acrylate, propyl(meth)acrylate and the like, propyl (meth)acrylate, trimethylcyclohexyl(meth)acrylate, methoxydiethylene glycol (meth)acrylate, ethoxydiethylene glycol (meth)acrylate, 3-methyltridecyl(meth)acrylate, 6-methyltridecyl(meth)acrylate, 7-methyltridecyl(meth) acrylate, 2,11-dimethyldodecyl(meth)acrylate, 2,7-dimethyl-4,5-diethyloctyl(meth)acrylate, pentadecyl(meth)acrylate, stearyl(meth)acrylate, stearyl(meth)acrylate, allyl (meth)acrylate and isobonyl(meth)acrylate.

An alkyl(meth)acrylate having a siloxane bond other than the silicone-containing monomer to be used in the present invention may also be used. Examples of the alkyl(meth) acrylate include straight-chain, branched or cyclic alkyl (meth)acrylates such as trimethylsiloxydimethylsilylmethyl (meth)acrylate, trimethylsiloxydimethylsilylpropyl(meth) acrylate, methylbis(trimethylsiloxy)silylpropyl(meth) acrylate, tris(trimethylsiloxy)silylpropyl(meth)acrylate, mono[methylbis(trimethylsiloxy)silylpropyl-(meth)acrylate], tris[methylbis(trimethylsiloxy)-silylpropyl(meth)acrylate], methylbis(trimethylsiloxy)silylpropylglyceryl-(meth) acrylate, tris(trimethylsiloxy)silylpropylglyceryl(meth) acrylate, mono[methylbis(trimethylsiloxy)siloxy]-bis (trimethylsiloxy)silylpropylglyceryl(meth)acrylate, trimethylsilylethyltetramethyldisiloxypropylglyceryl(meth) acrylate, trimethylsilylmethyl(meth)acrylate, trimethylsilylpropyl(meth)acrylate, trimethylsilylpropylglyceryl(meth) acrylate, trimethylsiloxydimethylsilylpropylglyceryl(meth) acrylate, methylbis(trimethylsiloxy)silylethyltetramethyldisiloxymethyl(meth)acrylate, tetramethyltriisopropylcyclotetrasiloxanylpropyl-(meth) acrylate, tetramethyltriisopropylcyclo-tetrasiloxybis(trimethylsiloxy)silylpropyl(meth)acrylate, (meth)acryloyloxypropyltrimethoxysilane, (meth) acryloyloxypropyltriethoxysilane, (meth) acryloyloxypropylmethyldimethylmethoxysilane, (meth) acryloyloxypropylmethyldimethoxysilane, (meth) acryloyloxypropylmethyldiethoxysilane, (meth) acryloyloxypropyldimethylmethoxysilane, (meth) acryloyloxypropyldimethylethoxysilane, (meth) acryloyloxyethyltrimethoxysilane, (meth) acryloyloxyethyltriethoxysilane, (meth) acryloyloxyethylmethyldimethoxysilane, (meth) acryloyloxyethylmethyldiethoxysilane, (meth) acryloyloxyethyldimethylmethoxysilane, (meth) acryloyloxyethyldimethylethoxysilane, (meth) acryloyloxymethyltrimethoxysilane, (meth) acryloyloxydimethyltriethoxysilane, (meth) acryloyloxymethylmethyldimethoxysilane, (meth) acryloyloxymethylmethyldiethoxysilane, (meth) acryloyloxymethyldimethylmethoxysilane, (meth) acryloyloxymethyldimethylethoxysilane and (meth) acryloyloxypropyltris(methoxyethoxy)silane.

In the present invention, a fluorine atom-containing alkyl (meth)acrylate which is generally known as a component used to improve the soil resistance of the surface of the lens and to decrease the adhesion of the surface of the lens may be compounded. Examples of the fluorine atom-containing alkyl (meth)acrylate include trifluoroethyl(meth)acrylate, tetrafluoropropyl(meth)acrylate, tetrafluoropentyl(meth)acrylate, hexafluorobutyl(meth)acrylate, hexafluorohexyl(meth) acrylate, hexafluorobis(trifluoromethyl)pentyl(meth) acrylate, hexafluoroisopropyl(meth)acrylate, heptafluorobutyl(meth)acrylate, octafluoropentyl(meth) acrylate, nonafluoropentyl(meth)acrylate, dodecafluoroheptyl(meth)acrylate, dodecafluorooctyl(meth)acrylate, tridecafluorooctyl(meth)acrylate, tridecafluoroheptyl(meth) acrylate, hexadecafluorodecyl(meth)acrylate, heptadecafluorodecyl(meth)acrylate, octadecafluoroundecyl (meth)acrylate, noadecafluoroundecyl(meth)acrylate, eicosafluorododecyl(meth)acrylate, 2-hydroxy-octafluoro-6-trifluoromethylheptyl(meth)acrylate, 2-hydroxy-dodecafluoro-8-trifluoromethylnonyl(meth)acrylate and 2-hydroxy-hexadecafluoro-10-trifluoromethylundecyl(meth)acrylate.

Generally, in the case of carrying out thermal polymerization and photopolymerization, a radical initiator, photosensitizer or the like is added to carry out these processes. Examples of the radical initiator include azo type initiators such as 2,2'-azobisisobutyronitrile, 1,1'-azobis(cyclohexane-1-carbonitrile), 2,2'-azobis(2,4-dimethylvaleronitrile), 2,2'-azobis(2-methylbutyronitrile), 2,2'-azobis(4-methoxy-2,4-dimethylvaleronitrile), dimethyl 2,2'-azobisbutylate and 2,2'-azobis(2,4,4-trimethylpentane) and organic peroxide type initiators such as diisobutyryl peroxide, di(3,5,5-trimethylhexanoyl) peroxide, dilauroyl peroxide, distearoyl peroxide, di-n-propylperoxydicarbonate, diisopropylperoxydicarbonate, di(4-tertiarybutylcyclohexyl)peroxydicarbonate, di(2-ethoxyethyl)peroxydicarbonate, di(2-ethylhexyl)peroxydicarbonate, di(3-methoxybutyl)peroxydicarbonate, cumylperoxyneodecanoate, 1,1,3,3-tetramethylbutylperoxyneodecanoate, 1-cyclohexyl-1-methylethylperoxyneodecanoate, tertiary hexylperoxyneodecanoate, tertiary butylperoxyneodecanoate, tertiary hexylperoxypivalate, tertiary butylperoxypivalate, 1,1,3,3-tetramethylbutylperoxy-2-ethylhexanoate, 2,5-dimethyl-2,5-di(2-hexanoyl)peroxyhexane, tertiary hexylperoxy-2-ethyl hexanoate, tertiary butylperoxy-2-ethyl hexanoate, tertiary butylperoxyisobutyrate, tertiary hexylperoxyisopropyl carbonate, tertiary butylperoxymaleic acid, tertiary butylperoxy-3,5,5-trimethyl hexanoate, tertiary butylperoxylaurate, 2,5-dimethyl-2,5-di(3-methylbenzoylperoxy)hexane, tertiary butylperoxyisopropyl carbonate, tertiary butylperoxy-2-ethylhexyl carbonate, tertiary hexylperoxy benzoate, 2,5-dimethyl2,5-di(benzoylperoxy)hexane, tertiary butylperoxyacetic acid and tertiary butylperoxy benzoate.

In the case of the composition of the present invention, the azo type initiator or organic oxide type initiator may be used. In this case, an initiator capable of initiating the polymerization reaction at a relatively low temperature, specifically, about 30 to 60° C. is preferably used. Since a vinyl carboxylate is compounded in the present invention, particularly the excellent characteristics of the present invention can be exhibited if a peroxy ester type organic peroxide type initiator is used and the use of this initiator is therefore desirable. Among these peroxy ester type organic peroxide initiators, a tertiary peroxy ester type such as a tertiary hexylperoxyneodecanoate, tertiary butylperoxyneodecanoate, tertiary hexylperoxypivalate or tertiary butylperoxypivalate type is particularly preferably used. If the organic peroxide type initiator and the azo type initiator are used together, it may be expected that polymerization with the acryl type monomer is more improved.

The amount of the initiator is preferably 0.001 to 1.0 parts by weight and more preferably 0.05 to 0.5 parts by weight based on 100 parts by weight of the copolymer component.

As a method of producing the ocular lens of the present invention, known methods such as a method in which the ingredients of the present invention are polymerized using a lens-shaped mold and a method in which the ingredients of the present invention are polymerized in a tube-shaped container and then cut and abraded into a lens form may be adopted. Also, in the case of utilizing the ingredients of the present invention as the ocular lens, it is possible to fit a lens support part to a lens part after a lens is formed or it is possible to integrate the lens part with the support part.

In the present invention, saponification treatment in which a vinyl carboxylate unit is alkali-treated into a vinyl alcohol unit is carried out to impart good wettability and hydrating properties to the obtained polymer. The saponification treatment is preferably carried out in an alkali solution. Examples of the alkaline compound to be used include sodium hydroxide, potassium hydroxide and calcium hydroxide. Among these compounds, sodium hydroxide is preferable. These alkaline compounds are preferably dissolved in water or alcohols when they are used. Examples of these alcohols include methanol, ethanol, propanol and butanol. Among these alcohols, methanol is preferably used in consideration of the swelling rate of the polymer in the saponification reaction and substitutional reactivity after the saponification treatment. In order to raise the effect of the saponification treatment, it is preferable to use an aqueous methanol solution having a sodium hydroxide concentration of preferably 0.1 to 10 parts by weight and more preferably 0.5 to 5.0 parts by weight. Also, the mixing ratio (methanol/water (ratio by volume)) of methanol to water in the aqueous methanol solution is preferably 30/70 to 90/10 and more preferably 50/50 to 80/20. The saponification treatment is carried out at a temperature of usually 0 to 100° C. and preferably 25 to 65° C. The treating time is preferably within a range of 30 to 360 minutes to carry out the treatment though depending on the concentration of the aqueous alcohol solution. When the time exceeds 360 minutes, hydrolysis of ester parts other than the vinyl carboxylate proceeds, bringing about dissociation of a silicone unit, which is a cause of reductions in oxygen permeability, strength and flexibility.

In the case of providing a ultraviolet absorbing effect to the ocular lens of the present invention, a ultraviolet absorber which is usually used may be added in the ingredients. Specific examples of the ultraviolet absorber include 2-hydroxy-4-(meth)acryloyloxybenzophenone, 2-hydroxy-4-(meth)acryloyloxy-5-t-butylbenzophenone, 2-(2'-hydroxy-5'-(meth)acryloyloxyethylphenyl)-2H-benzotriazole, 2-(2'-hydroxy-5'-(meth)acryloyloxyethylphenyl)-5-chloro-2H-benzotriazole and phenyl 2-hydroxy-4-methacryloyloxymethylbenzoate.

EXAMPLES

The present invention will be explained in detail by way of examples, which are not intended to be limiting of the present invention.

(Method of Evaluation)

As a method of evaluating each contact lens put into a swelled state in examples and comparative examples, the following tests and evaluation standards were adopted.

(Oxygen Transmission Coefficient)

For the evaluation of the oxygen transmission amount of the contact lens molded body, the oxygen transmission coefficient (Dk value) was measured based on "Working Procedures for Measurement of Dk value by Improved Electrode Method" described in Manual of Approval for Production and Import License for Contact Lens (Japan Contact Lens Association).

(Moisture Content)

For the evaluation of the contact lens molded body, the moisture content was measured based on "Measurement of Moisture Content of Hydrogel Lens (ISO 10339:1997)".

(Wettability of the Surface of the Lens)

The contact lens molded body was dipped in physiological brine kept at 37±2° C. for 24 hours and then, pulled up from the brine to evaluate the wettability of the surface of the lens visually.

⊙: The entire surface exhibits good wettability, showing that the surface has high moisture retaining ability.

○: Though it is confirmed that a part of the surface repels water, the surface exhibits good wettability, showing that the surface has high moisture retaining ability.

Δ: Though the entire surface exhibits good wettability, the surface lacks in the moisture retaining ability.

▲: It is confirmed that a part of the surface repels water and the surface lacks in the moisture retaining ability.

x: It is confirmed that the entire surface repels water.

(Elasticity and Strength of the Lens)

A test specimen was prepared according to "Method of Tensile Test of Plastic (JIS K 7113)" and a swelled test piece was used as a sample to measure the elasticity and strength. Moreover, after the obtained sample was treated at 121° C. for 20 minutes in a vial, the elasticity and strength of the sample were measured in the same manner as above and the resistance of the sample to hydrolysis was also evaluated.

(Lens Shape-Retaining Ability and Transparency)

The shape-retaining ability and transparency of the contact lens molded body were measured visually.

(Standard of Evaluation of the Shape of the Lens)

When the lens front side of the contact lens molded body was made to face downward and placed on the hand to observe from the side;

○: A bowl shape is retained.

Δ: A bowl shape is slightly opened.

x: No bowl shape can be retained.

(Standard of Evaluation of the Transparency of the Lens)

○: Perfectly transparent.

Δ: Partly clouded (milky white).

x: 50% or more is clouded.

Examples 1 to 3

Both terminal (meth)acryl polydimethylsiloxane (FM-7725 (manufactured by Chisso Corporation), n=130, m and p=3), vinyl acetate (Vac), N,N-dimethylacrylamide (DMAA), tridecylmethacrylate (TDMA) and triallylisocyanurate (TAIC) were mixed in the amounts shown in Table 1. Then, tertiary butylperoxypivalate (t-BuPV) was added to each mixture in an amount of 0.5 parts by weight.

After these ingredients were thoroughly stirred so as to obtain a uniform mixture, the mixture was injected into a polypropylene mold having a lens form and heated at 40° C. for 10 hours in a nitrogen atmosphere to make a polymer having a lens form. The saponification treatment of the obtained polymer was carried out in the following manner: 1% by weight of sodium hydroxide was added in an aqueous 75% methanol solution and the polymer was dipped at 40° C. for 60 minutes.

The results of the evaluation of the obtained lens molded bodies are shown in Table 1.

Examples 4 to 14

Both terminal (meth)acryl polydimethylsiloxane (FM-7725 (manufactured by Chisso Corporation), n=130, m and p=3), vinyl acetate (Vac) or vinyl butylate (VBu), N,N-dimethylacrylamide (DMAA), triallylisocyanurate (TAIC), tertiary butylmethacrylate (TBMA) and/or cyclohexylmethacrylate (CHMA) or benzylmethacrylate (BzMA), tridecylmethacrylate (TDMA) or laurylmethacrylate (LMA) and siloxanylmethacrylate (SiMA) or methylmethacrylate (MMA) were mixed in the amounts shown in Table 1. Then, tertiary butylperoxypivalate (t-BuPV) or tertiary butylperoxyneodecanoate (t-BuND) and azobisisobutyronitrile (AIBN) was added to each mixture in a total amount of 0.5 parts by weight, to manufacture a lens in the same procedures as in Example 1, which was then evaluated in the same procedures as in Example 1.

The results of the evaluation of the obtained lens molded bodies are shown in Table 1.

Examples 13 and 14 are examples which produce the crosslinking effect though the moisture content is dropped because FM-7725 is formulated in a larger amount than those of other examples.

Comparative Example 1

This is the case of using no N,N-dimethylacrylamide in the present invention. Specifically, a lens was manufactured using the composition shown in Table 2 and evaluated in the same procedures as in Example 1.

In the case of using no N,N-dimethylacrylamide, a saponification reaction did not proceed and therefore, good wettability could not obtained.

Comparative Example 2

The polymer obtained using the composition shown in Table 2 was used to manufacture a lens in the same procedures as in Example without carrying out saponification treatment and the obtained lens was evaluated. The results of the evaluation are shown in Table 2. The obtained lens was inferior in moisture content and the wettability of the surface thereof though it had high oxygen permeability, and it couldn't be used as an ocular lens.

Comparative Examples 3 and 4

A lens was manufactured using the composition shown in Table 2 in the same procedures as in Example 1 except that both terminal (meth)acryl polydimethylsiloxane (FM-7711 (manufactured by Chisso Corporation), n=8, m and p=3, or FM-7726 (manufactured by Chisso Corporation), n=250, m and p=3) was used in place of the both terminal (meth)acryl polydimethylsiloxane (FM-7725), n=130, m and p=3) and was evaluated. When FM-7711 having a smaller molecular weight than FM-7725 was used, the obtained lens had low oxygen permeability, whereas when FM-7726 having a larger molecular weight than FM-7725 was used, the polymer was clouded and the lens couldn't be used as an ocular lens.

TABLE 1

| | | | Example 1 | Example 2 | Example 3 | Example 4 | Example 5 | Example 6 | Example 7 |
|---|---|---|---|---|---|---|---|---|---|
| Composition | Monomer composition (parts by weight) | FM-7725 | 20 | 20 | 10 | 20 | 20 | 30 | 30 |
| | | FM-7711 | | | | | | | |
| | | FM-7726 | | | | | | | |
| | | VAc | 64 | 59 | 64 | 52 | 52 | 50 | |
| | | VBu | | | | | | | 50 |
| | | DMAA | 5 | 10 | 15 | 10 | 10 | 10 | 10 |
| | | TBMA | | | | 8 | | | 5 |
| | | CHMA | | | | | 8 | | |
| | | BzMA | | | | | | 5 | |
| | | TDMA | 10 | 10 | 10 | 9 | 9 | 4.5 | |
| | | LMA | | | | | | | 4.5 |
| | | MMA | | | | | | | |
| | | SiMA | | | | | | | |
| | | TAIC | 1 | 1 | 1 | 1 | 1 | 0.5 | 0.5 |
| | Polymeric Initiator | t-BuND | | | | 0.5 | 0.5 | 0.5 | 0.5 |
| | | t-BuPV | 0.5 | 0.5 | 0.5 | | | | |
| | | AIBN | | | | | | | |
| Results of evaluation | Saponification treatment (Saponified or non-saponified) | | Saponified | Saponified | Saponified | Saponified | Saponified | Saponified | Saponified |
| | Dk value* | | 205.44 | 200.78 | 114.89 | 151.65 | 160.00 | 165.52 | 162.23 |
| | Wettability of the surface of the lens | | ☉ | ☉ | ☉ | ☉ | ☉ | ☉ | ☉ |
| | Moisture content (%) | | 55.51 | 51.12 | 57.41 | 32.25 | 33.25 | 38.24 | 37.19 |
| | Rupture strength ($\times 10^5$ Pa) | | 2.29 | 2.24 | 1.98 | 4.00 | 3.55 | 3.95 | 3.85 |
| | Rupture strength after boiling ($\times 10^5$ Pa) | | 2.18 | 2.29 | 2.04 | 3.91 | 3.58 | 4.01 | 3.84 |
| | Rupture extension (%) | | 371.19 | 420.11 | 408.22 | 508.00 | 515.00 | 485.00 | 480.00 |
| | Rupture extension after boiling (%) | | 428.00 | 432.90 | 417.54 | 500.21 | 509.92 | 485.22 | 498.19 |
| | Shape retaining properties | | ☉ | ☉ | ☉ | ☉ | ☉ | ☉ | ☉ |
| | Transparency | | ○ | ○ | ○ | ○ | ○ | ○ | ○ |

TABLE 1-continued

|  |  |  | Example | | | | | | |
|---|---|---|---|---|---|---|---|---|---|
|  |  |  | 8 | 9 | 10 | 11 | 12 | 13 | 14 |
| Composition | Monomer composition (parts by weight) | FM-7725 | 30 | 25 | 25 | 25 | 30 | 50 | 50 |
|  |  | FM-7711 |  |  |  |  |  |  |  |
|  |  | FM-7726 |  |  |  |  |  |  |  |
|  |  | VAc |  |  |  | 45 |  |  |  |
|  |  | VBu | 50 | 48 | 50 |  | 50 | 30 | 30 |
|  |  | DMAA | 10 | 12 | 10 | 14.5 | 10 | 10 | 10 |
|  |  | TBMA | 2.5 | 5 | 5 | 5 | 5 | 5 | 3 |
|  |  | CHMA | 2.5 |  |  |  |  |  | 2 |
|  |  | BzMA |  |  |  |  |  |  |  |
|  |  | TDMA | 4.5 | 4.5 | 4.5 | 10 | 4.5 | 4.5 | 4.5 |
|  |  | LMA |  |  |  |  |  |  |  |
|  |  | MMA |  |  | 5 |  |  |  |  |
|  |  | SiMA |  |  |  | 5 |  |  |  |
|  |  | TAIC | 0.5 | 0.5 | 0.5 | 0.5 | 0.5 |  |  |
|  | Polymeric Initiator | t-BuND | 0.5 | 0.5 | 0.5 |  | 0.3 | 0.5 | 0.5 |
|  |  | t-BuPV |  |  |  | 0.5 |  |  |  |
|  |  | AIBN |  |  |  |  | 0.2 |  |  |
| Results of evaluation | Saponification treatment (Saponified or non-saponified) |  | Saponified | Saponified | Saponified | Saponified | Saponified | Saponified | Saponified |
|  | Dk value* |  | 150.88 | 125.00 | 145.23 | 140.00 | 138.60 | 157.11 | 160.46 |
|  | Wettability of the surface of the lens |  | ⊙ | ⊙ | ⊙ | ⊙ | ⊙ | ⊙ | ⊙ |
|  | Moisture content (%) |  | 34.44 | 31.88 | 31.00 | 32.00 | 31.55 | 28.44 | 25.49 |
|  | Rupture strength ($\times 10^5$ Pa) |  | 3.81 | 4.05 | 4.05 | 3.85 | 4.01 | 4.19 | 4.21 |
|  | Rupture strength after boiling ($\times 10^5$ Pa) |  | 3.75 | 4.11 | 3.88 | 3.83 | 3.92 | 4.10 | 4.24 |
|  | Rupture extension (%) |  | 501.20 | 407.25 | 475.00 | 500.00 | 487.93 | 410.97 | 404.22 |
|  | Rupture extension after boiling (%) |  | 497.98 | 401.52 | 469.95 | 502.11 | 477.21 | 408.89 | 401.83 |
|  | Shape retaining properties |  | ⊙ | ⊙ | ⊙ | ⊙ | ⊙ | ○ | ○ |
|  | Transparency |  | ○ | ○ | ○ | ○ | ○ | ○ | ○ |

*$\times 10^{-11}$(cm$^2$/sec) · (mLO$_2$/mL × mmHg)

TABLE 2

|  |  |  | Comparative Example | | | |
|---|---|---|---|---|---|---|
|  |  |  | 1 | 2 | 3 | 4 |
| Composition | Monomer composition (parts by weight) | FM-7725 | 20 | 20 |  |  |
|  |  | FM-7711 |  |  | 20 |  |
|  |  | FM-7726 |  |  |  | 20 |
|  |  | VAc | 69 | 54 | 54 | 54 |
|  |  | VBu |  |  |  |  |
|  |  | DMAA |  | 15 | 15 | 15 |
|  |  | TBMA |  |  |  |  |
|  |  | CHMA |  |  |  |  |
|  |  | BzMA |  |  |  |  |
|  |  | TDMA | 10 | 10 | 10 | 10 |
|  |  | LMA |  |  |  |  |
|  |  | MMA |  |  |  |  |
|  |  | SiMA |  |  |  |  |
|  |  | TAIC | 1 | 1 | 1 | 1 |
|  | Polymeric Initiator | t-BuND |  |  |  |  |
|  |  | t-BuPV | 0.5 | 0.5 | 0.5 | 0.5 |
|  |  | AIBN |  |  |  |  |
| Results of evaluation | Saponification treatment (Saponified or non-saponified) |  | Saponified | Non-Saponified | Saponified | Saponified |
|  | Dk value* |  | 184.23 | 207.44 | 60.24 | 301.80 |
|  | Wettability of the surface of the lens |  | X | X | ○ | ▲ |
|  | Moisture content (%) |  | 5.17 | 4.67 | 48.12 | 34.12 |
|  | Rupture strength ($\times 10^5$ Pa) |  | 2.44 | 2.01 | 2.07 | 2.58 |
|  | Rupture strength after boiling ($\times 10^5$ Pa) |  | 2.38 | 1.95 | 2.10 | 2.21 |
|  | Rupture extension (%) |  | 208.63 | 216.19 | 259.70 | 587.99 |

TABLE 2-continued

| | Comparative Example | | | |
|---|---|---|---|---|
| | 1 | 2 | 3 | 4 |
| Rupture extension after boiling (%) | 199.84 | 207.81 | 278.32 | 555.45 |
| Shape retaining properties | Δ | ⊙ | ○ | Δ |
| Transparency | ○ | ○ | ○ | X |

*×10$^{-11}$(cm$^2$/sec) · (mLO$_2$/mL × mm)

The abbreviations in Table 1 show the following compounds.

FM-7725, FM-7711 and FM-7226: Compounds represented by the following formula.

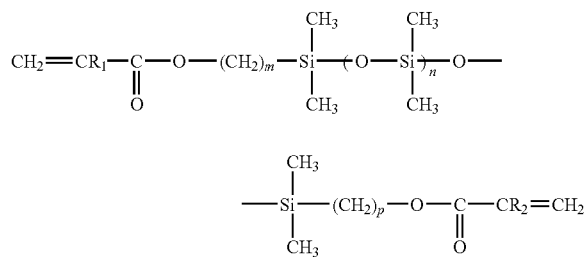

FM-7725: n=130, m and p=3, molecular weight 10000
FM-7711: n=8, m and p=3, molecular weight 1000
FM-7726: n=250, m and p=3, molecular weight 20000
VAc: Vinyl acetate
VBu: Vinyl butylate
DMAA: N,N-dimethylacrylamide
TBMA: Tertiary butylmethacrylate
CHMA: Cyclohexylmethacrylate
BzMA: Benzyl methacrylate
TDMA: Tridecylmethacrylate
MMA: Methylmethacrylate
LMA: Laurylmethacrylate
SiMA: Siloxanylmethacrylate
TAIC: Triallylisocyanurate
t-BuPV: Tertiary butylperoxypivalate (perbutyl PV)
t-BuND: Tertiary butylperoxyneodecanoate (perbutyl ND)
AIBN: Azobisisobutyronitrile

INDUSTRIAL APPLICABILITY

The present invention can provide an ocular lens which has good wettability of the surface thereof, oxygen permeability, transparency and shape recoverability, and is also superior in tensile strength and rupture extension relatively easily, though it has a composition using a silicone-containing monomer.

The invention claimed is:

1. An ocular lens obtained by saponifying a copolymer prepared from a both-terminal (meth)acryl polydimethylsiloxane represented by the following formula (1), a vinyl carboxylate, a (meth)acrylamide type monomer and a monomer copolymerizable with these compounds:

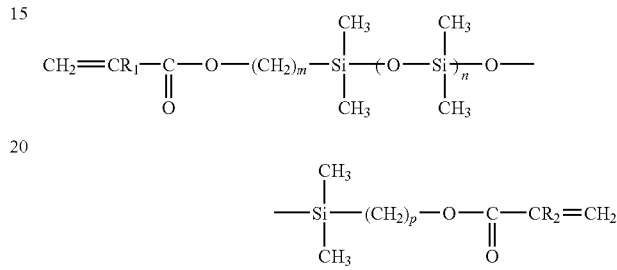

wherein $R_1$ and $R_2$ respectively represent a hydrogen atom or a methyl group, m and p respectively denote an integer from 1 to 5 and n denotes an integer from 10 to 150, wherein the ocular lens is oxygen-permeable and hydrated, and wherein the moisture content of the ocular lens is about 25.49% to 57.41%.

2. An ocular lens obtained by saponifying a copolymer prepared from a both-terminal (meth)acryl polydimethylsiloxane represented by the following formula (1), a vinyl carboxylate, a (meth)acrylamide type monomer, a vinyl type crosslinking agent and a monomer copolymerizable with these compounds:

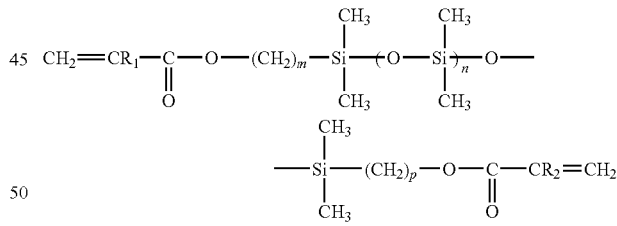

wherein $R_1$ and $R_2$ respectively represent a hydrogen atom or a methyl group, m and p respectively denote an integer from 1 to 5 and n denotes an integer from 10 to 150 wherein the ocular lens is oxygen-permeable and hydrated, and wherein the moisture content of the ocular lens is about 31.00% to 57.41%.

3. An ocular lens obtained by saponifying a copolymer prepared from a both-terminal (meth)acryl polydimethylsiloxane represented by the following formula (1), a vinyl carboxylate, a (meth)acrylamide type monomer, one or both of a (meth)acrylate having a tertiary structure and a (meth)acrylate having a cyclic structure and a monomer copolymerizable with these compounds:

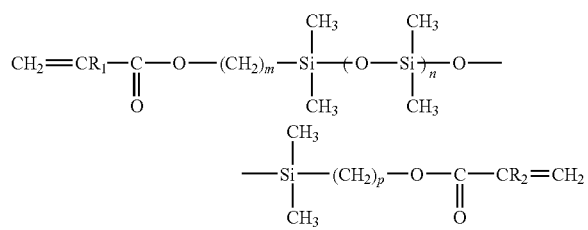

wherein $R_1$ and $R_2$ respectively represent a hydrogen atom or a methyl group, m and p respectively denote an integer from 1 to 5 and n denotes an integer from 10 to 150 wherein the ocular lens is oxygen-permeable and hydrated, and wherein the moisture content of the ocular lens is about 25.49% to 38.24%.

4. An ocular lens obtained by saponifying a copolymer prepared from a both-terminal (meth)acryl polydimethylsiloxane represented by the following formula (1), a vinyl carboxylate, a (meth)acrylamide type monomer, a vinyl type crosslinking agent, one or both of a (meth)acrylate having a tertiary structure and a (meth)acrylate having a cyclic structure and a monomer copolymerizable with these compounds: wherein $R_1$ and $R_2$ respectively represent a hydrogen atom or a methyl group, m and p

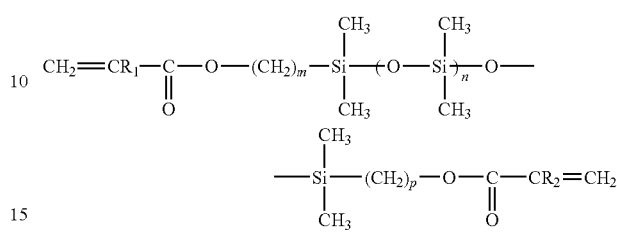

respectively denote an integer from 1 to 5 and n denotes an integer from 10 to 150 wherein the ocular lens is oxygen-permeable and hydrated, and wherein the moisture content of the ocular lens is about 31.00% to 38.24 %.

* * * * *